US00PP21806P2

(12) United States Plant Patent
Jacobs

(10) Patent No.: US PP21,806 P2
(45) Date of Patent: Mar. 22, 2011

(54) *ALSTROEMERIA* PLANT NAMED 'ZAPRIARI'

(50) Latin Name: *Alstroemeria hybrida*
Varietal Denomination: Zapriari

(75) Inventor: Henricus Cornelius Maria Jacobs, Rijsenhout (NL)

(73) Assignee: Van Zanten Plants b.v., Hillegom (NL)

( * ) Notice: Subject to any disclaimer, the term of this patent is extended or adjusted under 35 U.S.C. 154(b) by 15 days.

(21) Appl. No.: 12/462,110

(22) Filed: Jul. 29, 2009

(51) Int. Cl.
*A01H 5/00* (2006.01)

(52) U.S. Cl. ..... Plt./309

(58) Field of Classification Search ..... Plt./309
See application file for complete search history.

(56) References Cited

PUBLICATIONS upov rom gtitm computer database, gti jouve retrieval software 2010/03 citation for 'Zapriari'.*

* cited by examiner

*Primary Examiner*—Wendy C. Haas
(74) *Attorney, Agent, or Firm*—C. A. Whealy

(57) ABSTRACT

A new and distinct cultivar of *Alstroemeria* plant named 'Zapriari', characterized by its upright, somewhat outwardly spreading and mounded plant habit; vigorous growth habit; yellow orange-colored flowers; and good container and garden performance.

1 Drawing Sheet

Botanical designation: *Alstroemeria hybrida.*
Cultivar denomination: 'ZAPRIARI'.

BACKGROUND OF THE INVENTION

The present invention relates to a new and distinct cultivar of *Alstroemeria* plant, botanically known as *Alstroemeria hybrida*, commercially used as a garden-type *Alstroemeria* plant, and hereinafter referred to by the name 'Zapriari'.

The new *Alstroemeria* plant is a product of a planned breeding program conducted by the Inventor in Rijsenhout, The Netherlands. The objective of the breeding program is to create new garden-type *Alstroemeria* cultivars with uniform plant habit, freely flowering habit, attractive foliage and flower coloration and excellent garden performance.

The new *Alstroemeria* plant originated from a cross-pollination made by the Inventor in Rijsenhout, The Netherlands in June, 2002, of a proprietary *Alstroemeria hybrida* selection identified as code number 00-0023-01, not patented, as the female, or seed, parent with a proprietary *Alstroemeria hybrida* selection identified as code number 87-1069-02, not patented, as the male, or pollen, parent. The new *Alstroemeria* plant was discovered and selected by the Inventor as a single flowering plant from within the progeny of the stated cross-pollination in a controlled greenhouse environment in Rijsenhout, The Netherlands in May, 2003.

Asexual reproduction of the new *Alstroemeria* plant by rhizome divisions in a controlled greenhouse environment in Rijsenhout, The Netherlands since September, 2003, has shown that the unique features of this new *Alstroemeria* plant are stable and reproduced true to type in successive generations.

SUMMARY OF THE INVENTION

Plants of the new *Alstroemeria* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Zapriari'. These characteristics in combination distinguish 'Zapriari' as a new and distinct cultivar of *Alstroemeria:*

1. Upright, somewhat outwardly spreading and mounded plant habit.
2. Vigorous growth habit.
3. Yellow orange-colored flowers.
4. Good container and garden performance.

Plants of the new *Alstroemeria* differ primarily from plants of the female parent selection in flower color as plants of the female parent selection have pink-colored flowers.

Plants of the new *Alstroemeria* differ primarily from plants of the male parent selection in flower color as plants of the male parent selection have yellow-colored flowers. In addition, plants of the new *Alstroemeria* are not as compact as plants of the male parent selection.

Plants of the new *Alstroemeria* can be compared to plants of *Alstroemeria hybrida* 'Staprioxa', disclosed in U.S. Plant Pat. No. 14,075. In side-by-side comparisons conducted in Rijsenhout, The Netherlands, plants of the new *Alstroemeria* differed primarily from plants of 'Staprioxa' in flower color as plants of 'Staprioxa' had flowers that are red purple in color. In addition, plants of the new *Alstroemeria* had larger flowers than plants of 'Staprioxa'.

BRIEF DESCRIPTION OF THE PHOTOGRAPH

The accompanying colored photograph illustrates the overall appearance of the new *Alstroemeria* plant, showing the colors as true as it is reasonably possible to obtain in colored reproductions of this type. Colors in the photograph may differ slightly from the color values cited in the detailed botanical description which accurately describe the colors of the new *Alstroemeria* plant. The photograph comprises a side perspective view of a typical flowering plant of 'Zapriari' grown in a container.

DETAILED BOTANICAL DESCRIPTION

The aforementioned photograph and following observations and measurements describe plants of the new *Alstroemeria* grown during the late summer in 14-cm containers in a glass-covered greenhouse in Rijsenhout, The Netherlands. During the production of the plants, day temperatures ranged from 15° C. to 25° C., night temperatures ranged from 10° C. to 15° C. and light levels averaged 5,000 lux. Plants were six months old when the photograph and the description were taken. In the following description, color references are made to The Royal Horticultural Society Colour Chart, 1995 Edition, except where general terms of ordinary dictionary significance are used.

Botanical classification: *Alstroemeria hybrida* 'Zapriari'.

Parentage:

*Female, or seed, parent.*—Proprietary *Alstroemeria hybrida* selection identified as code number 00-0023-01, not patented.

*Male or pollen parent.*—Proprietary *Alstroemeria hybrida* selection identified as code number 87-1069-02, not patented.

Propagation:

*Type.*—In vitro rhizogenesis.

*Time to produce a rooted young plant, summer.*—About 40 days.

*Time to produce a rooted young plant, winter.*—About 60 days.

*Root description.*—Fibrous, fleshy, thick; close to 155D in color.

*Rooting habit.*—Freely branching; moderately dense.

*Rhizomes.*—Shape: Elongate; rounded. Length: About 10 cm to 30 cm. Diameter: About 3 mm to 10 mm. Texture: Smooth. Color: Close to 155D.

Plant description:

*Plant and growth habit.*—Upright, somewhat outwardly spreading and mounding plant habit; freely branching habit, bushy appearance; vigorous growth habit.

*Plant height.*—About 25 cm to 30 cm.

*Plant diameter (spread).*—About 25 cm.

Lateral branch description:

*Aspect.*—Mostly upright.

*Length.*—About 9.5 cm to 12 cm.

*Diameter.*—About 2 mm to 3 mm.

*Internode length.*—About 3 mm to 4 mm.

*Strength.*—Strong.

*Texture.*—Smooth, glabrous.

*Color.*—Close to 146D.

Foliage description:

*Appearance.*—Leaves asymmetrical; sessile.

*Length.—l About* 9.7 cm to 12 cm.

*Width.*—About 2.4 cm to 3.6 cm.

*Shape.*—Lanceolate.

*Apex.*—Acute.

*Base.*—Cuneate.

*Margin.*—Entire, undulate.

*Texture, upper and lower surfaces.*—Smooth, glabrous.

*Venation pattern.*—Parallel.

*Color.*—Developing and fully expanded leaves, upper surface: Close to 146A; venation, close to 141D. Developing and fully expanded leaves, lower surface: Close to 137C; venation, close to 137D.

Flower description:

*Flower type and habit.*—Single cup-shaped flowers arranged in compound umbels; flowers face mostly outwardly; perianth segments separate; freely flowering habit.

*Natural flowering season.*—Flowering continuous during the spring in The Netherlands.

*Fragrance.*—None detected.

*Flower longevity on the plant.*—About four weeks; flowers not persistent.

*Flower buds.*—Length: About 4.5 cm to 5 cm. Diameter: About 1.3 cm to 1.5 cm. Shape: Roughly ovoid. Color: Close to 179A.

*Umbel height.*—About 9.5 cm to 12 cm.

*Umbel diameter.*—About 15 cm to 16 cm.

*Number of flowers per umbel.*—Potentially about 25.

*Flower diameter.*—About 6.5 cm.

*Flower length (height).*—About 6 cm.

*Flower depth.*—About 6 cm to 6.5 cm.

*Perianth.*—Arrangement: Six arranged in two whorls, each whorl with two lateral and one median segments. Outer perianth, lateral segments: Length: About 5.4 cm to 5.9 cm. Width: About 3.3 cm to 3.9 cm. Shape: Obovate. Apex: Embedded pointed. Base: Attenuate. Margin: Entire; weakly undulate. Texture, upper and lower surfaces: Smooth, glabrous. Color, when opening and fully opened, upper surface: Close to 15B; color becoming closer to 15C with development. Color, when opening and fully opened, lower surface: Close to 15B and 179B. Outer perianth, median segment: Length: About 5.4 cm to 6 cm. Width: About 3.3 cm to 4 cm. Shape: Obovate. Apex: Embedded pointed. Base: Attenuate. Margin: Entire; weakly undulate. Texture, upper and lower surfaces: Smooth, glabrous. Color, when opening and fully opened, upper surface: Close to 15B; color becoming closer to 15C with development. Color, when opening and fully opened, lower surface: Close to 15B and 179B. Inner perianth, lateral segments: Length: About 5.7 cm to 6.4 cm. Width: About 1.9 cm to 2.3 cm. Shape: Oblanceolate. Apex: Wishbone-shaped. Base: Attenuate. Margin: Entire; slightly undulate. Texture, upper and lower surfaces: Smooth, glabrous. Color, when opening and fully opened, upper surface: Close to 14B; color becoming closer to 15C with development. Color, when opening and fully opened, lower surface: Close to 14B and 179B. Inner perianth, median segment: Length: About 5.3 cm to 5.9 cm. Width: About 1.9 cm to 2.3 cm. Shape: Oblanceolate. Apex: Wishbone-shaped. Base: Attenuate. Margin: Entire; slightly undulate. Texture, upper and lower surfaces: Smooth, glabrous. Color, when opening and fully opened, upper surface: Close to 14B; color becoming closer to 15C with development. Color, when opening and fully opened, lower surface: Close to 14B and 179B.

*Peduncles.*—Length: About 1.5 to 4.5 cm. Diameter: About 2 mm to 3 mm. Strength: Strong. Angle: Erect to about 30° from vertical. Texture: Smooth, glabrous. Color: Close to 146D.

*Reproductive organs.*—Stamens: Quantity per flower: Six. Anther shape: Elliptical. Anther length: About 7 mm to 8 mm. Anther color: Close to 152A. Pollen amount: Moderate. Pollen color: Close to 152A. Pistils: Quantity per flower: One. Style length: About 3.2 cm to 4.5 cm. Style color: Close to 29B. Stigma shape: Three-parted. Stigma color: Close to 31B. Ovary color: Close to 146D.

*Fruit/seed.*—Fruit and seed development has not been observed.

Disease/pest resistance: Plants of the new *Alstroemeria* have not been observed to be resistant to pathogens and pests common to *Alstroemeria*.

Garden performance: Plants of the new *Alstroemeria* have been observed to have good garden performance and to tolerate wind, rain and temperatures from about −5° C. to about 40° C.

It is claimed:

1. A new and distinct *Alstroemeria* plant named 'Zapriari' as illustrated and described.

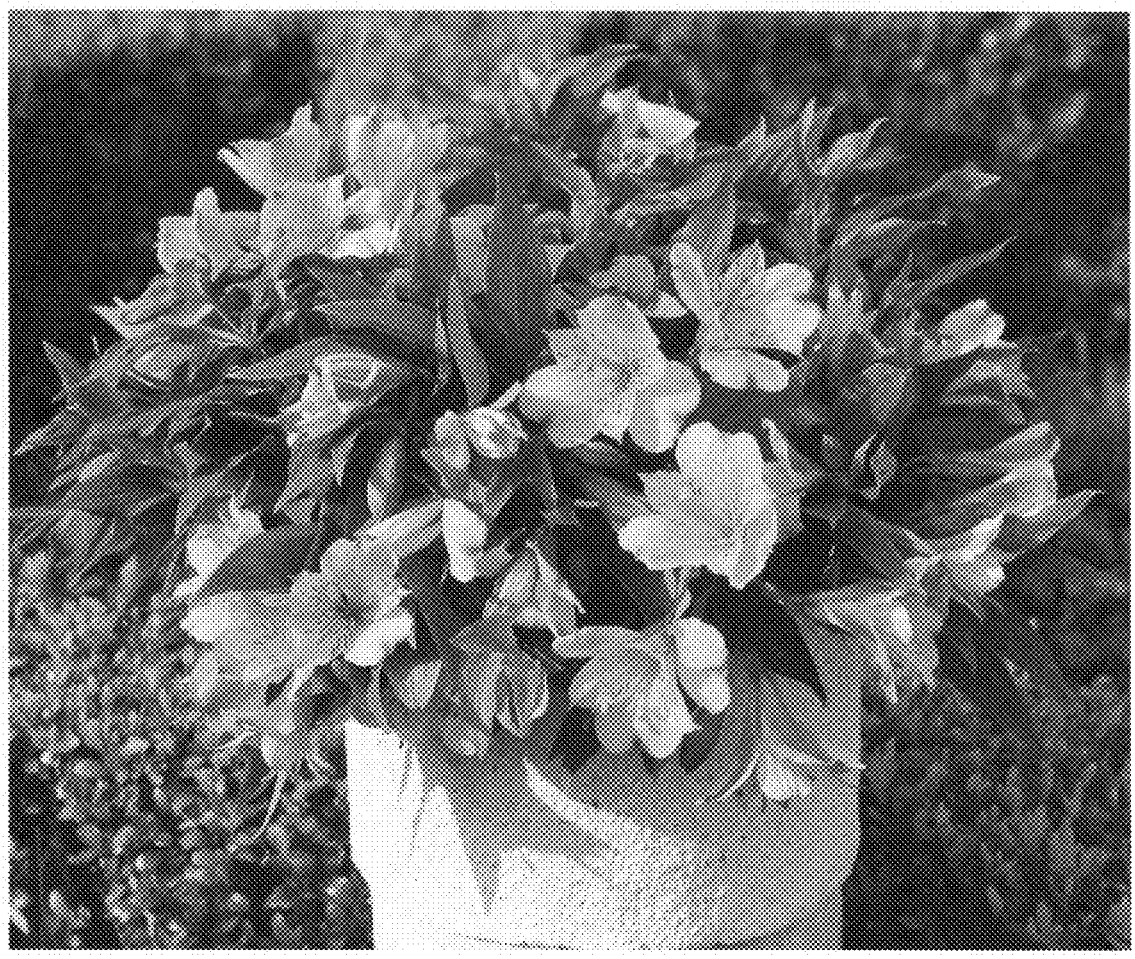

* * * * *